United States Patent [19]

Nakamura et al.

[11] Patent Number: 5,035,245
[45] Date of Patent: Jul. 30, 1991

[54] ULTRASONIC DOPPLER BLOOD FLOW VELOCITY DETECTION APPARATUS

[75] Inventors: Yasuhiro Nakamura, Tokyo; Ikuo Sakai, Kawasaki; Masami Kawabuchi, Yokohama, all of Japan

[73] Assignee: Matsushita Electric Industrial Co., Ltd., Japan

[21] Appl. No.: 355,944

[22] Filed: May 22, 1989

[30] Foreign Application Priority Data

May 23, 1988 [JP] Japan .............................. 63-125285

[51] Int. Cl.$^5$ .............................................. A61B 8/06
[52] U.S. Cl. .......................... 128/661.09; 73/861.25
[58] Field of Search .................... 128/661.07–661.09; 73/861.25

[56] References Cited

U.S. PATENT DOCUMENTS

| 4,534,357 | 8/1985 | Powers ............................ 128/661.09 |
| 4,780,837 | 10/1988 | Namekawa ......................... 364/565 |
| 4,807,636 | 2/1989 | Skidmore et al. ............... 128/661.10 |

FOREIGN PATENT DOCUMENTS 0166392 1/1986 European Pat. Off. .
8801850 3/1988 PCT Int'l Appl. .

OTHER PUBLICATIONS

Namekawa, K. et al., "Doppler Signal Frequency Converter", EP 0166392, published 2/1/86.
Sainz, A. et al., "PLL Techniques Applied to UTS Doppler Signal Processing", *Ultrasonics* vol. 14, No. 3 May 1976.

*Primary Examiner*—Francis Jaworski
*Attorney, Agent, or Firm*—Lowe, Price, LeBlanc & Becker

[57] ABSTRACT

An ultrasonic Doppler blood flow detection apparatus of the invention comprises: a transducing circuit for emitting ultrasonic waves at a predetermined interval and for receiving reflected ultrasonic waves from an object in the blood vessel and converting the received signal into an electric echo signal; a frequency-difference signal producing circuit for producing frequency-difference components between the echo signal and first pair of quadrature signals of a frequency f1 in response to the echo signal and the first pair of quadrature signals; first and second Doppler signal detection circuit for detecting first and second Doppler signals of upper and lower sidebands of the frequency f1 from the frequency-difference components in response to second pair of quadrature signals of a frequency f2; and a frequency difference calculation circuit for calculating frequency difference between output signals from the first and second Doppler signal detection circuits. The frequency difference indicates compressed Doppler shift frequency which can detect a higher velocity of blood flow.

9 Claims, 5 Drawing Sheets

ULTRASONIC DOPPLER BLOOD FLOW VELOCITY DETECTION APPARATUS

BACKGROUND OF THE INVENTION

1. Field of the Invention

This invention relates to an ultrasonic Doppler blood flow velocity detection apparatus.

2. Description of the Prior Art

An ultrasonic Doppler blood flow velocity detection apparatus is used for detecting blood flow velocity which can be used in diagnoses. There are many types of Doppler blood flow detection apparatus utilizing Doppler effect through reflection of ultrasonic waves. The ultrasonic Doppler blood flow velocity detector can select a portion where blood flow is to be detected with respect to distance and direction.

The most popular ultrasonic Doppler blood flow velocity detection apparatus detects blood flow velocity as follows:

Such an ultrasonic Doppler blood flow velocity detection apparatus transmits an ultrasonic-wave pulse whose center frequency is "f", at a predetermined interval into the human body by a transducer; then it receives a reflected signal, i.e., an echo signal, from a moving reflective object, such as a blood corpuscle; and detects the amount of phase shift of the echo signal, i.e., Doppler shift. An output signal of the phase shift amount, i.e. Doppler signal, indicates blood flow velocity.

In this conventional Doppler blood flow velocity detection apparatus, the relation between a shift frequency fd of a Doppler signal and blood flow velocity V is given by:

$$fd = (2V/c) \cdot f \cos \theta \qquad (1)$$

where "c" is a sound velocity in the human body; $\theta$ is an angle made between the ultrasonic transmitting direction and the direction of blood flow, wherein the shift frequency fd is subjected to a limitation given by:

$$|fd| \leq fp/2 \qquad (2)$$

where fp is a repetition frequency of ultrasonic-wave pulses (also referred to as a rate frequency).

The Doppler shift frequency fd should not exceed a half of the frequency fp because of the sampling theory. If blood velocity V exceeds a velocity corresponding to ultrasonic-wave pulse repetition frequency fp, the ultrasonic Doppler blood flow velocity detection apparatus outputs incorrect velocity and direction. Particularly, if a deep portion is measured, period of time from transmission of an ultrasonic-wave pulse to reception of the reflected ultrasonic waves by a sensor of the apparatus becomes long. Then, the frequency fp of the ultrasonic-wave pulse should be set at a low value. Therefore, it is difficult to detect a high velocity of blood flow.

An ultrasonic Doppler blood velocity detecting apparatus is disclosed in U.S. Pat. No. 4,534,357, which is provided to moderate the above-mentioned limitation of measurable blood flow velocity.

FIG. 7 is a block diagram of the above-mentioned disclosed ultrasonic Doppler blood velocity detecting apparatus. In FIG. 7, the device 210 of the apparatus includes standard Doppler system 212 (shown within dashed lines). The standard Doppler system 212 includes a master oscillator 214 and a transmitter 216 which transmits signals through a transducer 218. Signals received from the transducer 218 are passed through a receiver amplifier 220 and through a first multiplier 222 which multiplies the received signal by COS $2\pi f1$. The signal resulting from that multiplication goes through a low pass filter 224, a sample-and-hold circuit 226, and a high pass filter 228 into a mean frequency estimator 230. Similarly, the received signal from receiver 220 are passed through a multiplier 232 which multiplies them by SIN $2\pi f1$ and the resulting signal is then sent through a low pass filter 234, a sample-and-hold circuit 236, and a high pass filter 238 into the mean frequency estimator 230.

The signals from the receiver 220 are also passed through a multiplier 242 where they are multiplied by COS $2\pi f2$. Those signals are then sent through a low pass filter 244, a sample-and-hold circuit 246, and a high pass filter 248 into a mean frequency estimator 250. Similarly, received signals from receiver 220 are multiplied in multiplier 252 by SIN $2\pi f2$ and sent into a low pass filter 254, a sample-and-hold circuit 256, and a high pass filter 258 into a mean frequency estimator 250. The outputs of the mean frequency estimators 230, 250 are sent into a subtractor 260 to obtain the unaliased mean frequency on output line 290.

Referring now to FIG. 8, the method of generating the sinusoidal waves corresponding to COS $2\pi f1$, SIN $2\pi f1$, SIN $2\pi f2$, and COS $2\pi f2$ on lines 223, 233, 253, and 243, respectively, are shown. In particular, outputs from the master oscillator 214, which is made to oscillate at a frequency of 4 nmp$\times$PRF (pulse repetition frequency of ultrasonic signal), where n, m and p are integers, are sent into a divide-by-n circuit 262 to obtain an output frequency corresponding to 4f1 on a line 263. Similarly, outputs from the master oscillator 214 are sent through a divide-by-m circuit 274 to obtain a signal corresponding to 4f2 on line 275, and into a divide-by-4 nmp circuit 286 to obtain a signal on line 288 which corresponds to PRF.

As mentioned above, the Doppler blood velocity flow detection apparatus of U.S. Pat. No. 4,534,357 is provided for extending a measurable maximum blood flow velocity by compressing Doppler shift frequency by obtaining Doppler signal frequencies which are detected with different reference frequencies. However, there is a drawback that the frequency of the master oscillator becomes too high. For example, if Doppler signals of $\pm 500$ KHz is obtained from an echo signal having a center frequency of 5 MHz, f1=4.5 MHz and f2=5.5 MHz, the frequency of the master oscillator 214 should be 198 MHz because n=11 and m=9.

Ultrasonic Doppler blood flow velocity detection apparatus in currently used are so designed that their repetition frequency of ultrasonic pulses can be changed. For example, if three frequencies of ultrasonic pulses are provided for such an apparatus, three sets of reference signals are required in addition to repetition frequency for ultrasonic pulse generation. Therefore, six frequencies of reference signals are necessary. The frequency of the master oscillator would become further high because the frequency is determined by a factor four times a common denominator of these six frequencies.

In a diagnosis of blood flow velocity with the above-mentioned prior art ultrasonic Doppler blood flow velocity detection apparatus, the blood flow velocities which are different from each other in accordance with a portion of a human body to be measured. It is necessary to determine the frequencies f1 and f2 in accordance with a blood flow velocity. When a low velocity of blood flow is measured, a difference between f1 and f2 should be set relatively large; when a high velocity of a blood flow is measured, the difference between f1 and f2 to be small. Therefore, there is a drawback that the frequency of the master oscillator is required to have a very high frequency for providing flexibly setting of the frequencies f1 and f2.

SUMMARY OF THE INVENTION

The present invention has been developed in order to remove the above-described drawbacks inherent to the conventional ultrasonic Doppler blood flow velocity detection apparatus.

According to the present invention there is provided an ultrasonic Doppler blood flow velocity detection apparatus comprising: a signal producing circuit responsive to a clock signal for producing pulses at a predetermined interval, and for producing first and second pairs of quadrature signals having different frequencies f1 and f2 respectively; a transducer for transmitting ultrasonic waves in response to each of the pulses and for receiving reflected ultrasonic waves from an ultrasonic-wave reflective object in the blood of a human body and converting the received ultrasonic waves into an electric echo signal; frequency-difference component producing circuit responsive to the echo signal and the first pair of quadrature signals for producing frequency-difference components indicative of frequency difference between the echo signal and the first pair of quadrature signals respectively; a first Doppler signal detecting circuit for detecting Doppler signal in a given frequency range within an upper sideband of the frequency f1 from the frequency-difference components in response to the second pair of quadrature signals; a second Doppler signal detecting circuit for detecting Doppler signal in another given frequency range within an lower sideband of the frequency f2 from the first and second components in response to the second pair of quadrature signals; and a frequency difference calculating circuit for calculating frequency difference between output signals from the first and second Doppler signal detecting circuit.

BRIEF DESCRIPTION OF THE DRAWINGS

The object and features of the present invention will become more readily apparent from the following detailed description taken in conjunction with the accompanying drawings in which.

The same or corresponding elements or parts are designated at like references throughout the drawings.

DETAILED DESCRIPTION OF THE INVENTION

Figure 1:
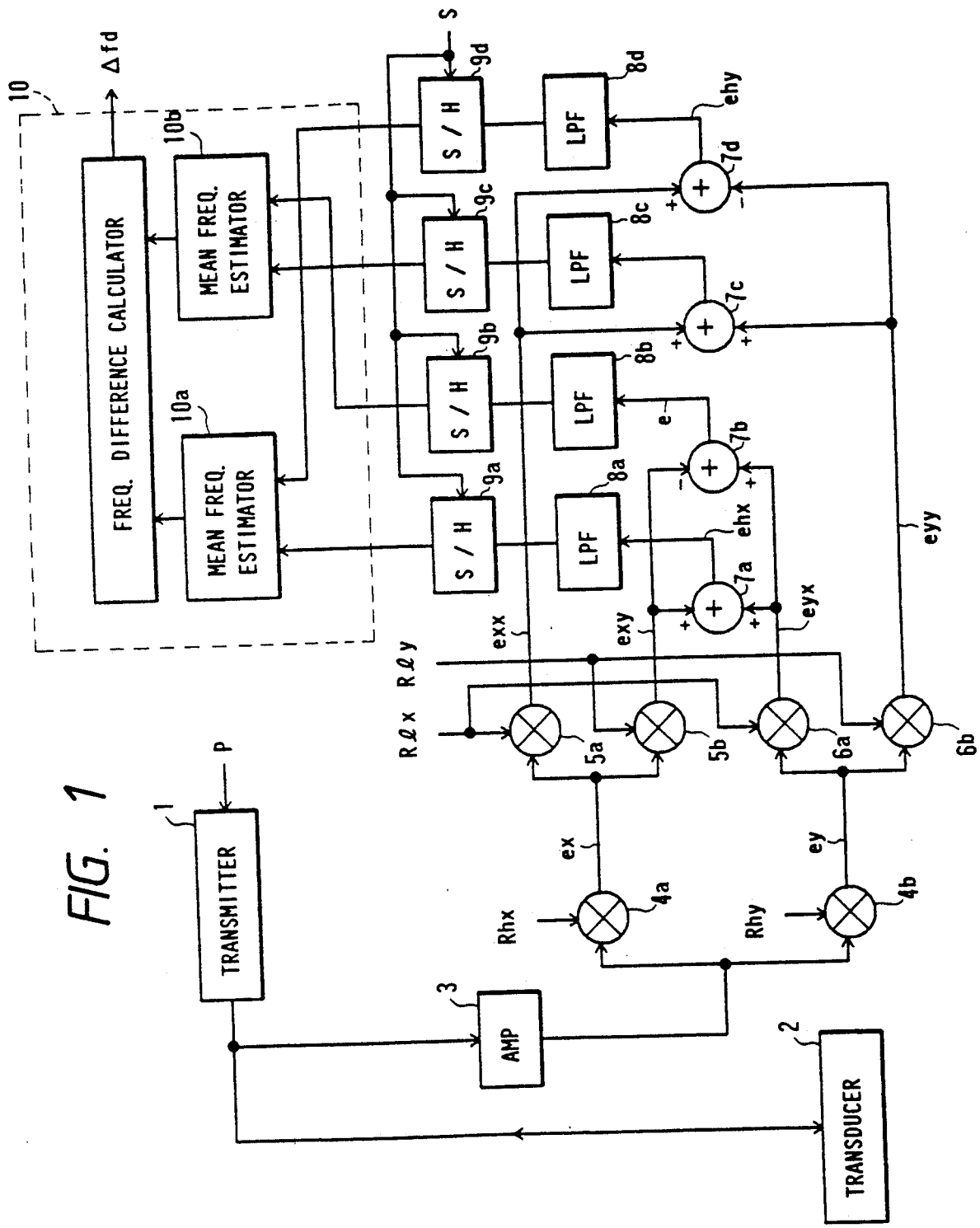
FIG. 1 is a block diagram of an Ultrasonic Doppler blood flow velocity detection apparatus of the invention.

Referring now to the drawings, FIG. 1 is a block diagram of an ultrasonic Doppler blood flow velocity detection apparatus of the invention.

Figure 2:
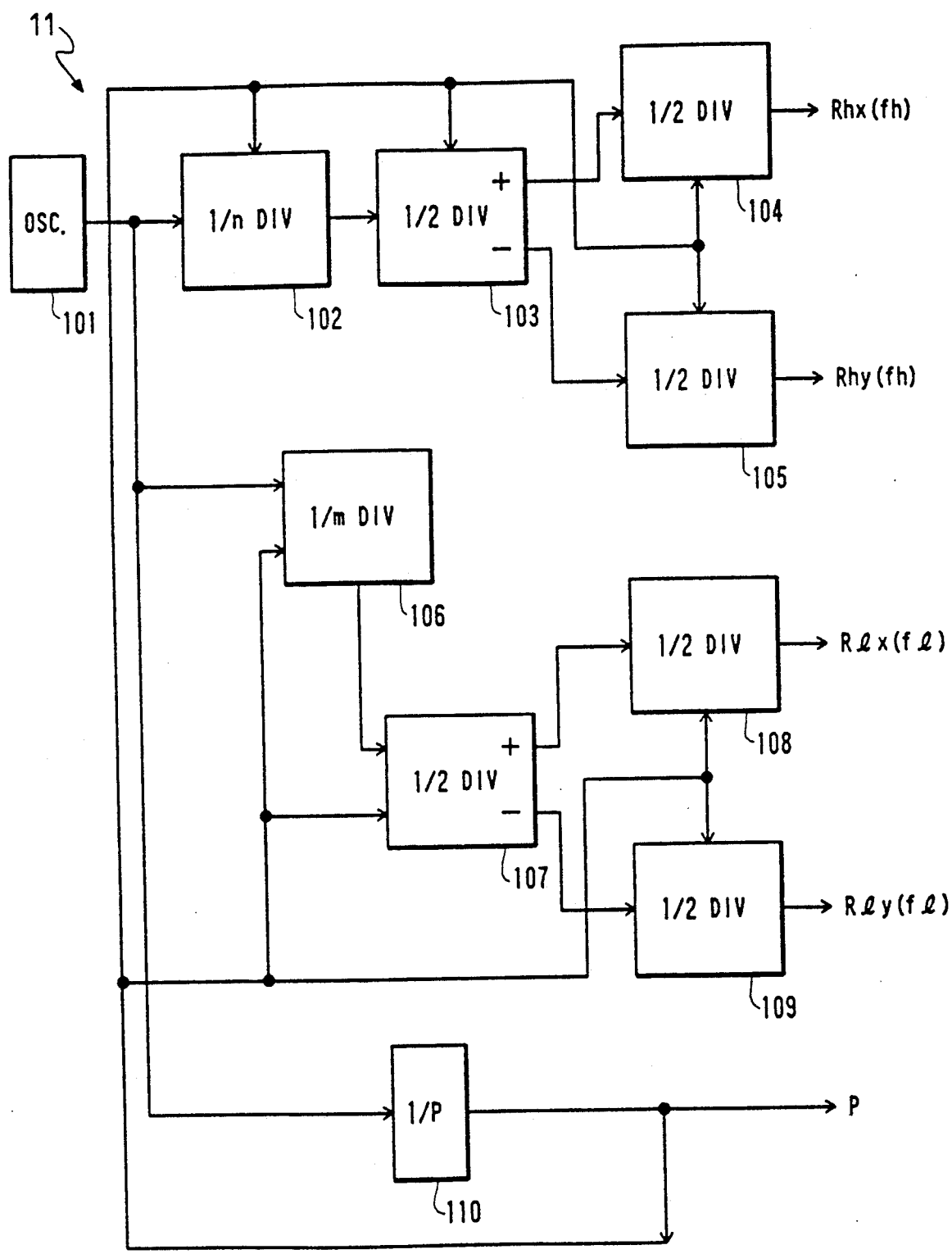
FIG. 2 is a block diagram of a clock circuit for producing clocks applied to the ultrasonic doppler blood velocity detection circuit of FIG. 1.

In FIG. 1, a transmitter 1 produces a drive signal in response to a signal P which is generated by a clock circuit 11 of FIG. 2. The drive signal is applied to a transducer 2 which outputs an ultrasonic-wave signal in response to the drive signal. The ultrasonic-wave signal transmitted from the transducer 2 is reflected at an object, such as a blood corpuscle in the blood vessel. The reflected ultrasonic-wave signal is received by the transducer 2. The transducer 2 converts the reflected and received ultrasonic-wave signal into an electric signal which will be referred to as an echo signal "e". The echo signal "e" is sent to an amplifier 3 which amplifies the echo signal "e" with a predetermined gain in order to obtain a desired output level. An output signal of the amplifier 3 is sent to a first set of two multipliers 4a and 4b. The multiplier 4a multiplies the echo signal "e" by a reference signal Rhx. The multiplier 4b multiplies the echo signal "e" by a reference signal Rhy. Frequency of the reference signal Rhx equals that of the reference signal Rhy and these reference signals have a phase difference of 90° therebetween. The signals Rhx and Rhy are also referred to as a pair of quadrature reference signals. The multipliers 4a and 4b produce frequency-difference components indicative of frequency difference between a pair of quadrature signals Rhx and Rhy from the echo signal "e" respectively. An output signal $e_x$ of the multiplier 4a is sent to a second set of multipliers 5a and 5b. An output signal $e_y$ of the multiplier 4b is sent to a third set of multipliers 6a and 6b. The multipliers 5a and 5b multiply the echo signals $e_x$ by a pair of quadrature reference signal Rlx and Rly respectively. An output signal $e_y$ of the multiplier 4b is sent to a third set of multipliers 6a and 6b. Frequency of the reference signal Rlx equals that of the reference signal Rly and these reference signals have a phase difference of 90° therebetween. The reference signals Rlx and Rly are also referred to as a pair of quadrature reference signals. Similarly, the echo signal $e_y$ is multiplied by the reference signals Rlx and Rly with the multipliers 6a and 6b respectively. An output signal $e_{xx}$ of the multiplier 5a is applied to an adder 7c and a subtractor 7d. The adder 7c adds the signal $e_{xx}$ to an output signal $e_{yy}$ of the multiplier 6b. The subtractor 7d subtracts the signal $e_{yy}$ from the signal $e_{xx}$. A set of signals from the adder 7c and subtractor 7d is a first Doppler signal. An output signal $e_{xy}$ of the multiplier 5b is sent to an adder 7a and a subtractor 7b. The adder 7a adds the signal $e_{xy}$ to an output signal $e_{yx}$ of the multiplier 6a. The subtractor 7b subtracts the signal $e_{xy}$ from the signal $e_{yx}$. Another set of signals from the adder 7c and subtractor 7d is a second Doppler signal. Output signals of the adder 7a, subtractor 7b, adder 7c, and subtractor 7d are sent to low-pass filters (LPF) 8a, 8b, 8c, and 8d respectively which remove high frequency components therefrom. Output signals of the low-pass filters 8a, 8b, 8c, and 8d are sent to sample-and-hold circuits 9a, 9b, 9c, and 9d respectively which sample and hold their input signals in response to a signal S respectively. A portion in a human body to be measured is determined by the time difference between timings of the signals P and S. Output signals of the sample-and-hold circuits 9a and 9d are sent to a known mean frequency estimator 10a which detects a first Doppler signal of the upper sideband of the frequency fh. Output signals of the sample-and-hold circuits 9b and 9c are sent to another mean frequency estimator 10b which detects a second Doppler signal of the lower sideband of the frequency fh. Each of the mean frequency estimators 10a and 10b averages frequency of their inputs signals to output a voltage signal. If a mean frequency increases, the sign of the voltage signal is plus; decreases, minus. If a mean frequency is constant, the voltage signal is zero volt. The plus sign means that the reflective object is moving toward the transducer, i.e., the later one of the two successive Doppler signals reaches the transducer in a shorter time than the former. The minus sign means that the reflective object is moving away from the transducer, i.e., the later one of the two successive Doppler signals reaches the transducer in a longer time than the former. The sign of the output signal of the mean frequency estimator 10a is same as that of the mean frequency estimator 10b. If the object is at rest, the voltage of the voltage signal is zero. The voltage signals of the mean frequency estimators 10a and 10b are sent to a known frequency difference calculator 10c which calculates the frequency difference between the voltage signals from the mean frequency estimators 10a and 10b and outputs a signal Δfd indicative of the frequency difference with a sign which is determined by the sign of the voltage signals of either frequency estimators 10a and 10b.

Hereinbelow will be described the operation of the ultrasonic Doppler blood flow velocity detection apparatus of the invention.

The echo signal contains various frequency components. The first set of multipliers 4a and 4b detects a component of a center frequency fh from the echo signal. The second and third sets of multipliers 5a, 5b, 6a, and 6b detect components of upper and lower sidebands, wherein frequency deviation from the center frequency fh to the upper and lower sideband is fl. Frequency components (fh+fl) and (fh−fl) of the echo signal are given by:

$$e = A[\sin\{(\omega h - \omega l)(t + \Delta t)\} + \sin\{(\omega h + \omega l)(t + \Delta t)\}] \quad (10)$$

where $\omega h = 2\pi fh$, $\omega l = 2\pi fl$; "A" is amplitude; "t" is time; t=0 means that an ultrasonic-wave pulse is transmitted; and Δt is a change in propagation of ultrasonic waves caused from the movement of an object.

Figure 3:
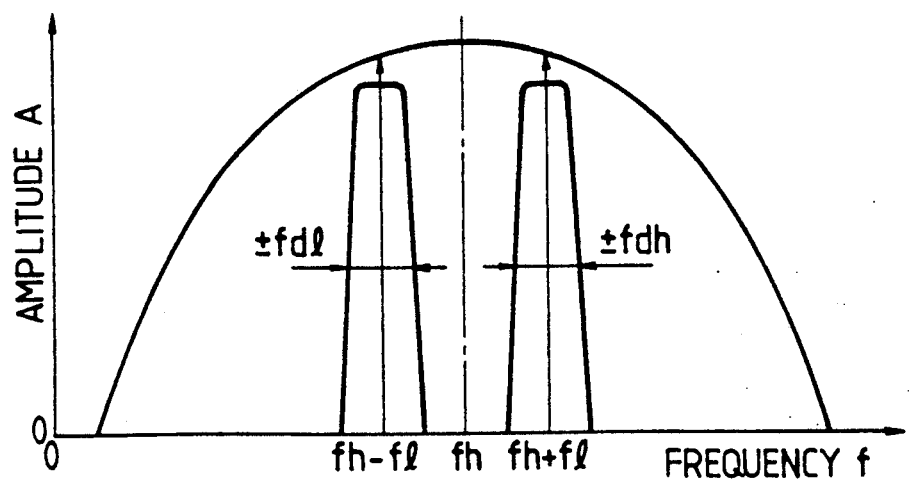
FIGS. 3, 4, 5, and 6 are frequency spectrum charts for illustrating operation of the ultrasonic Doppler blood flow velocity detection apparatus of FIG. 1.

Frequency spectrum according to Eq. (10) is shown in FIG. 3. In FIG. 3, two frequency components (fh+fl) and (fh−fl) contain Doppler shift components ±fdh and ±fdl. The first a pair of quadrature reference signals Rhx and Rhy are given by:

$$Rhx = 1 \cdot \cos(\omega h \cdot t) \quad (11)$$
$$Rhy = 1 \cdot \sin(\omega h \cdot t)$$

where "1" is amplitude; and "t" is time.

The multipliers 4a and 4b perform a balanced modulation, i.e., multiply the echo signal "e" by the a pair of quadrature reference signals Rhx and Rhy. The outputs signal $e_x$ and $e_y$ are:

$$\begin{aligned} e_x &= e \cdot Rhx \\ &= A/2\ [-\sin\{\omega l \cdot t - (\omega h - \omega l)\Delta t\} + \\ &\quad \sin\{\omega l \cdot t + (\omega h + \omega l)\Delta t\}] \end{aligned} \quad (12)$$

$$\begin{aligned} e_y &= e \cdot Rhy \\ &= A/2\ [-\cos\{\omega l \cdot t - (\omega h - \omega l)\Delta t\} + \\ &\quad \cos\{\omega l \cdot t + (\omega h + \omega l)\Delta t\}] \end{aligned} \quad (13)$$

where only difference frequency components between the echo signal and respective a pair of quadrature reference signals Rhx and Rhy are given.

Figure 4:
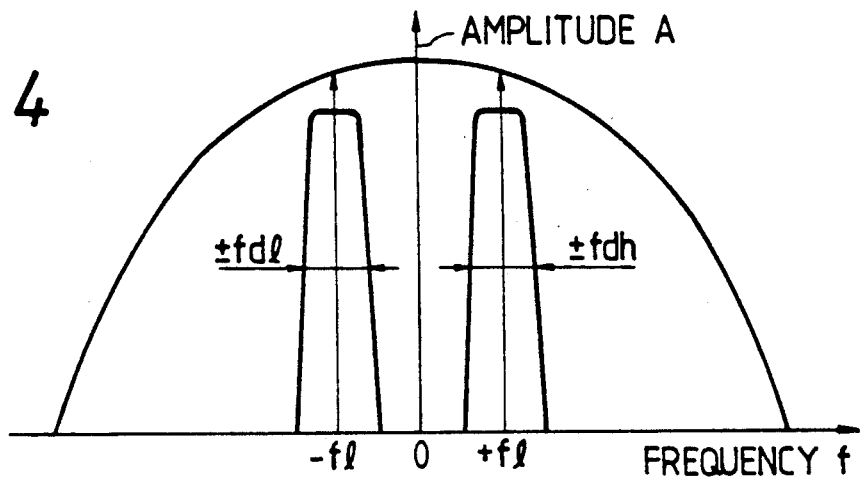

Frequency spectrums according to Eq. (12) and (13) are shown in FIG. 4. In FIG. 4, the two component signals are symmetrically shown about an amplitude axis. In the upper sideband there is the Doppler signal fdh which extends around the frequency +fl. In the lower sideband there is the Doppler signal fdl around the frequency −fl.

The second and third sets of multipliers 5a, 5b, 6a, and 6b, adders 7a and 7c, and subtractors 7b and 7c separate and detect the Doppler signals fdh and fdl. The second set of multipliers 5a and 5b detects quadrature components from the signal $e_x$ given by Eq. (12) with the a pair of quadrature reference signals Rlx and Rly. The third set of multipliers 6a and 6b detects quadrature components from the signal $e_y$ given by Eq. (13) with the a pair of quadrature reference signals Rlx and Rly. The a pair of quadrature reference signals Rlx and Rly are given by:

$$Rlx = 1 \cdot \cos(\omega l \cdot t) \quad (14)$$
$$Rly = 1 \cdot \sin(\omega l \cdot t)$$

The output signals $e_{xx}$ and $e_{xy}$ of the multipliers 5a and 5b are given by:

$$\begin{aligned} e_{xx} &= e_x \cdot Rlx \\ &= (A/4)\ [\sin\{(\omega h - \omega l)\Delta t\} + \\ &\quad \sin\{\omega h + \omega l)\Delta t\}] \end{aligned} \quad (15)$$

$$\begin{aligned} e_{xy} &= e_x \cdot Rly \\ &= (A/4)[-\cos\{(\omega h - \omega l)\Delta t\} + \\ &\quad \cos\{\omega h + \omega l)\Delta t\}] \end{aligned} \quad (16)$$

The output signals $e_{yx}$ and $e_{yy}$ of the multipliers 6a and 6b are given by:

$$\begin{aligned} e_{yx} &= e_y \cdot Rlx \\ &= (A/4)\ [\cos\{(\omega h - \omega l)\Delta t\} + \\ &\quad \cos\{\omega h + \omega l)\Delta t\}] \end{aligned} \quad (17)$$

$$\begin{aligned} e_{yy} &= e_y \cdot Rly \\ &= (A/4)[\sin\{(\omega h - \omega l)\Delta t\} - \\ &\quad \sin\{\omega h + \omega l)\Delta t\}] \end{aligned} \quad (18)$$

Eq. (15) to Eq. (18) exhibit only difference frequency components between $e_x$ and Rlx, $e_x$ and Rly, $e_y$ and Rlx, and $e_y$ and Rly. The adder 7c adds the signal $e_{xx}$ given by Eq. (15) to the signal $e_{yy}$ given by Eq. (18). The subtractor 7d subtracts the signal $e_{yy}$ from the signal $e_{xx}$. The adder 7a adds the signal $e_{xy}$ given by Eq. (16) to the signal $e_{yx}$ given by Eq. (17). The subtractor 7b subtracts the signal $e_{xy}$ from the signal $e_{yx}$. The output signals of the adder 7a and subtractor 7d are given by:

$$ehx = e_{yx} + e_{xy} \quad (19)$$
$$= (A/2) \cdot \cos\{(\omega h + \omega l)\Delta t\}$$

$$ehy = e_{xx} - e_{yy}$$
$$= (A/2) \cdot \sin\{(\omega h + \omega l)\Delta t\}$$

The output signals of the subtractor 7b and adder 7c are given by:

$$elx = e_{yx} - e_{xy} \quad (20)$$
$$= (A/2) \cdot \cos\{(\omega h - \omega l)\Delta t\}$$

$$ehy = e_{xx} + e_{yy}$$
$$= (A/2) \cdot \sin\{(\omega h - \omega l)\Delta t\}$$

Figure 5:
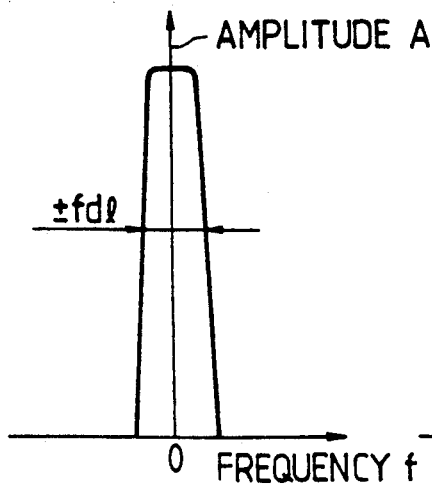
Figure 6:
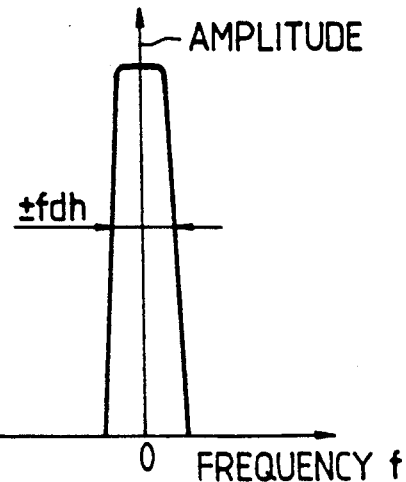
Figure 7:
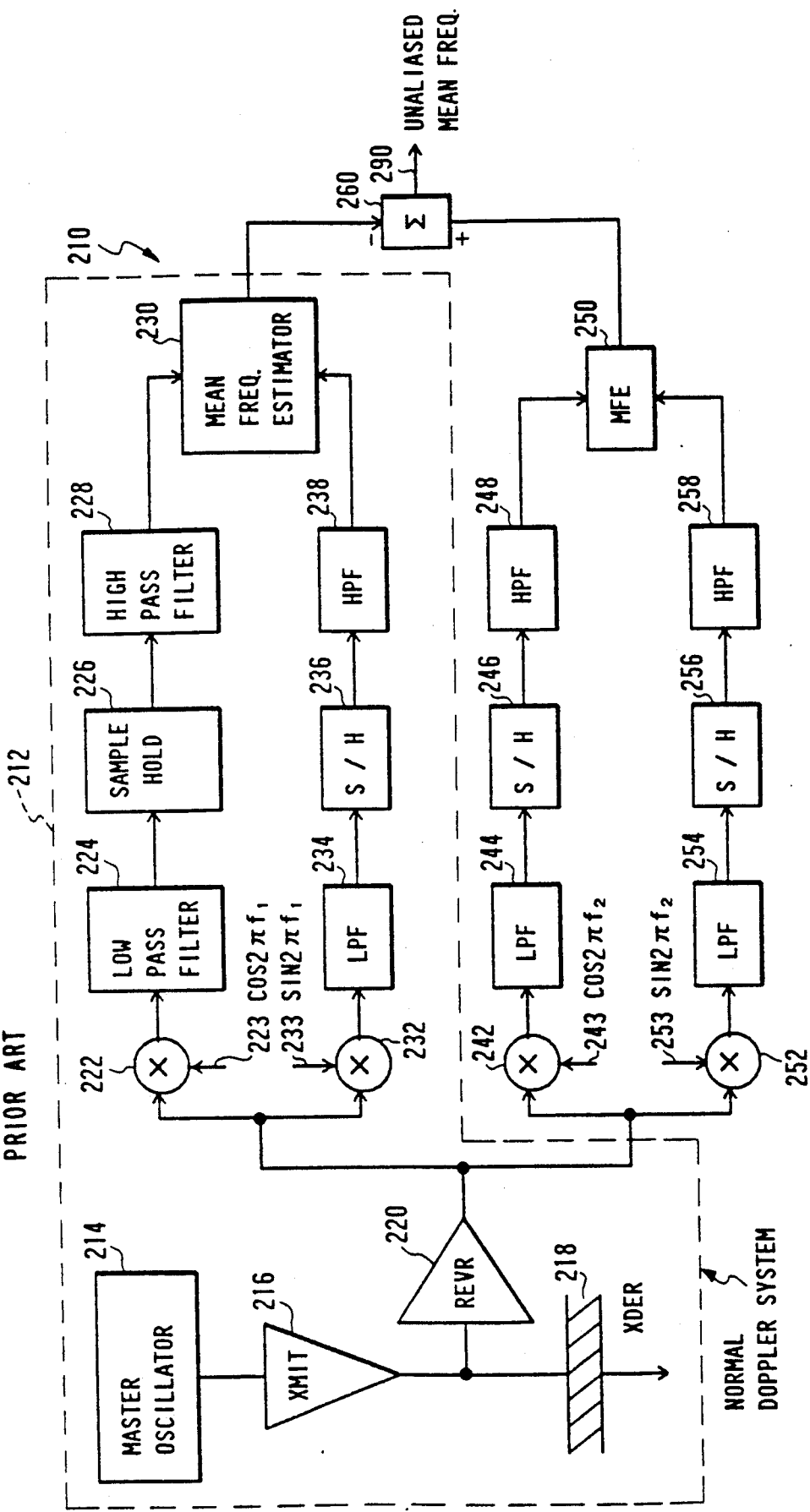
FIG. 7 is a block diagram of prior art ultrasonic Doppler blood velocity detection apparatus.
Figure 8:
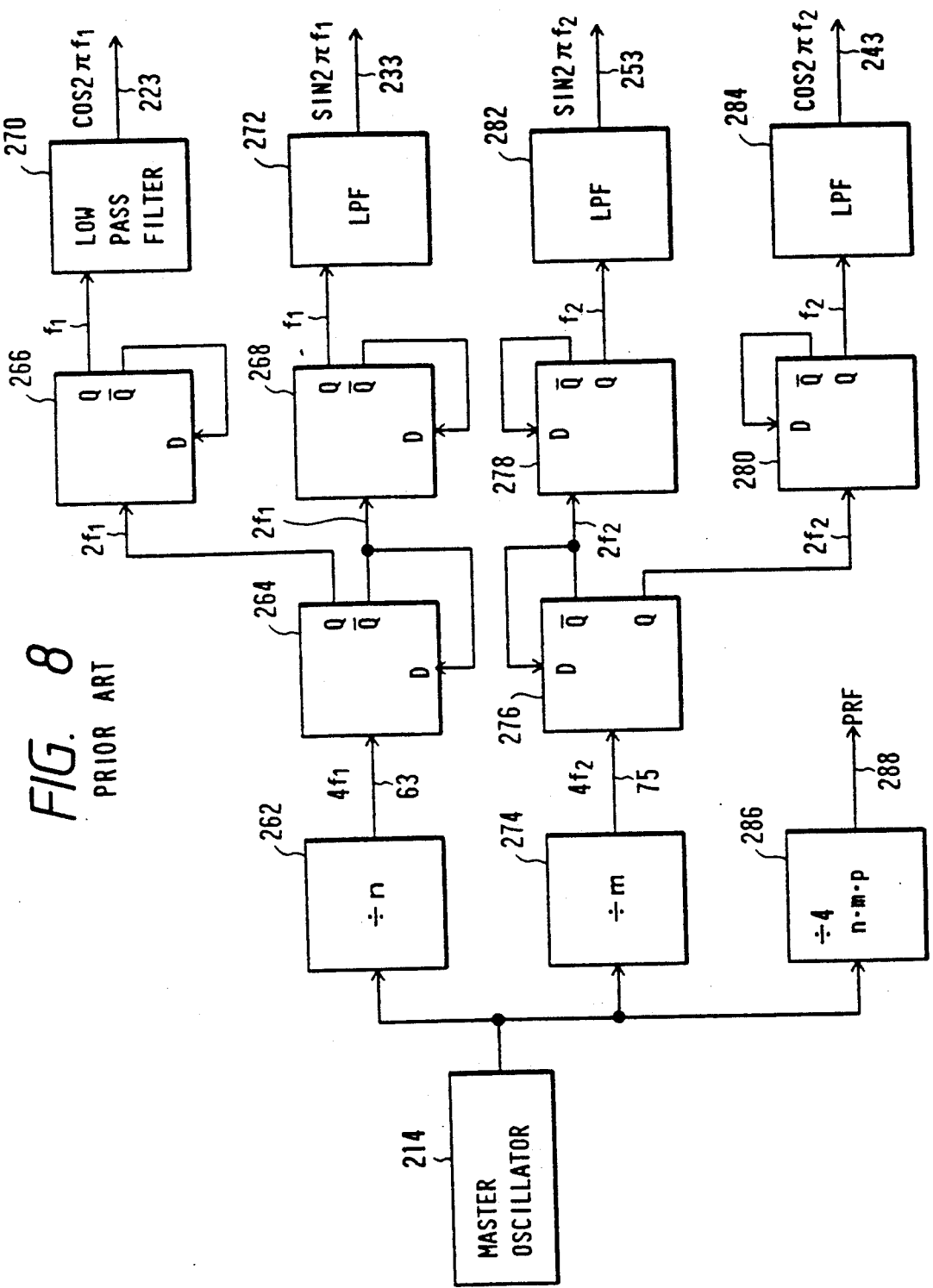
FIG. 8 is a block diagram of a clock circuit for producing clocks applied to the ultrasonic doppler blood velocity detection circuit of FIG. 7.

Eq. (19) shows the first Doppler signal around the frequency (fh+fl). The frequency spectrum of the first Doppler signal is shown in FIG. 6. Eq. (20) shows the second Doppler signal around the frequency (fh−fl). The frequency spectrum of the second Doppler signal is shown in FIG. 5. In this way frequency components of fdh and fdl are separated and detected.

The low-pass filters 8a, 8b, 8c, and 8d remove undesired high frequency components from these Doppler signals. The sample-and-hold circuits 9a, 9b, 9c, and 9d sample the Doppler signals from the portion in a human body to be measured in response to the signal S wherein an interval between the ultrasonic signal and the signals S is determined by the distance between the portion and the transducer.

Assuming that the Doppler shift angular frequency of Eq. (19) is $\omega dh$; and the Doppler shift angular frequency of Eq. (20) is $\omega dl$, the Doppler shift signals are detected by the mean frequency estimator 10a and 10b and they are given by:

$$\omega dh = (\omega h + \omega l)\Delta t/Tp \quad (21)$$
$$\omega dl = (\omega h - \omega l)\Delta t/Tp$$

where $\Delta t/Tp$ is variation $\Delta t$ per one repetition period of time Tp of transmission of ultrasonic-wave pulses.

The frequency difference calculator 10c produces signal $\Delta \omega d$ from the Doppler shift signals $\omega dh$ and $\omega dl$ which are given by:

$$\Delta \omega d = \omega dh - \omega dl \quad (22)$$
$$= 2 \cdot \omega l \cdot \Delta t/Tp$$

Assuming that a sound velocity in a human body is "c"; the velocity of the reflective object is "v"; an angle made between the direction of transmitting of ultrasonic waves and the movement of the reflective object is $\theta$, $\Delta t$ is given by:

$$\Delta t = 2 \cdot (v/c) \cdot Tp \cdot \cos\theta \quad (23)$$

$\Delta fd$ is given by substituting Eq. (22) for Eq. (23) as follows:

$$\Delta fd = (2 \cdot v/c) \cdot (2 \cdot fl) \cos\theta \quad (24)$$

The frequencies fh and fl are set in accordance with the relation:

$$fh > fl/2$$

The frequency fh is set to be a frequency around the center frequency of the echo signal. In this way, $\Delta fd$ can be compressed compared with fd of Eq. (1).

FIG. 2 is a block diagram of a clock circuit for generating a first a pair of quadrature reference signals Rhx, Rhy, second a pair of quadrature reference signals Rlx, Rly, and the signal P. A clock signal of frequency $f_o$ is produced by an oscillator 101. The clock signal is divided by "n" with a divider 102, and further divided by "2" with a divider 103. The divider 103 has an inverting output "−" and non-inverting output "+" which have an inverting relation each other. The output "+" is divided by "2" with a divider 104. The output "−" is divided by "2" with a divider 105. In this way, the a pair of quadrature reference signals Rhx and Rhy of a frequency "fh" have a phase difference of 90° therebetween.

The clock signal from the oscillator 101 is also sent to a divider 106 which divides the clock signal by "m". An output signal of the divider 106 is divided by "2" with a divider 107. The divider 107 has an inverting output "−" and non-inverting output "+" which have an inverting relation each other. The output "+" is divided by "2" with a divider 108. The output "−" is divided by "2" with a a divider 109. In this way, the a pair of quadrature reference signals Rlx and Rly of a frequency "fl" have a phase difference of 90° therebetween.

The clock signal from the oscillator 101 is further sent to a divider 110 which divides the clock signal by "p" to output the signal P. The signal P resets dividers 102–109 to synchronize the first a pair of quadrature reference signals Rhx, Rhy, and second a pair of quadrature reference signal Rlx, Rly therewith.

In the ultrasonic Doppler blood flow velocity detection apparatus, if a center frequency of ultrasonic waves is set at 5 MHz which is the same as that of the prior art ultrasonic Doppler blood flow velocity to obtain a Doppler shift frequency difference $\Delta fd$ between Doppler signals detected at +500 KHz and −500 KHz, the frequency fh of the first a pair of quadrature reference signals Rhx and Rhy is set to 5 MHz and the frequency of the second a pair of quadrature reference signals Rlx and Rly is set at 500 KHz. In the clock circuit, a frequency of an output signal of the divider 102 should be set to 20 MHz and a frequency of an output signal of the divider 106 should be set to 2 MHz. Therefore, n:m=1:10. If n=1, the frequency of the oscillator 101 should be 20 MHz for a minimum frequency because m=10.

In this invention, the Doppler shift frequency can be obtained with compression thereof. The lower frequency fl, i.e., larger value of "m", makes compression of the Doppler shift frequency large. Thus, the frequency of the oscillator does not become too high. In addition, if a transducer of different frequency is used, the frequency fh can be changed by changing "n". On the other hand, in the ultrasonic Doppler blood flow velocity detection apparatus of the prior art smaller frequency difference between two a pair of quadrature reference signals f1 and f2 makes compression of Doppler shift frequency large. Thus the frequency of the oscillator becomes too high.

As mentioned above, in the ultrasonic Doppler blood flow velocity detection apparatus of the invention the echo signal received by the transducer 2 is modulated.

Doppler shift signals of upper and lower sidebands are detected from the modulated signals. The Doppler shift frequency is compressed by the frequency difference between these two Doppler shift signals. Therefore, a high velocity of a blood flow can be detected by a relatively low frequency of the oscillator 101 and thus, the circuit arrangement becomes simple. Further, in the transmission and processing of ultrasonic-wave signal, the frequency of the ultrasonic waves and repetition frequencies can be changed in accordance with a portion to be measured or a transducer to be used. Accordingly, the ultrasonic Doppler blood flow velocity of the invention can be more widely applied to blood flow velocity detection of difficult circumstances than the prior art ultrasonic blood flow velocity detection apparatus.

What is claimed is:

1. An ultrasonic Doppler blood flow velocity detection apparatus comprising:
    (a) signal producing means responsive to a clock signal for producing pulses at a predetermined interval, and for producing first and second pairs of quadrature signals having different frequencies f1 and f2 respectively;
    (b) transducing means for transmitting ultrasonic waves in response to each of said pulses and for receiving reflected ultrasonic waves from an ultrasonic-wave reflective object in the blood of a human body and converting the received ultrasonic waves into an electric echo signal;
    (c) frequency-difference component producing means responsive to said echo signal and said first pair of quadrature signals for producing frequency-difference components indicative of frequency differences between said echo signal and each of said first pair of quadrature signals respectively;
    (d) first Doppler signal detecting means for detecting a Doppler signal in a given frequency range within an upper sideband of said frequency f1 from said frequency-difference components in response to said second pair of quadrature signals;
    (e) second Doppler signal detecting means for detecting a Doppler signal in another given frequency range within a lower sideband of said frequency f2 from said frequency-difference components in response to said second pair of quadrature signals; and
    (f) frequency difference calculating means for calculating frequency difference between output signals from said first and second Doppler signal detecting means;
    wherein said frequency f1 is substantially equal to a center frequency of said ultrasonic waves from said transducing means and frequency f2 is determined to provide a desired measurement range of a velocity of said object.

2. An ultrasonic Doppler blood flow velocity detection apparatus as claimed in claim 1, wherein said frequency-difference component producing means comprises first and second multipliers for multiplying said echo signal by said first pair of quadrature signals, respectively.

3. An ultrasonic Doppler blood flow velocity detection apparatus as claimed in claim 2, wherein said first Doppler signal detecting means comprises:
    (a) a third multiplier for multiplying an output signal of said first multiplier by a first signal of said second pair of quadrature signals;
    (b) a fourth multiplier for multiplying an output signal of said first multiplier by a second signal of said second pair of quadrature signals;
    (c) a fifth multiplier for multiplying an output signal of said second multiplier by said first signal of said second pair of quadrature signals;
    (d) a sixth multiplier for multiplying an output signal of said second multiplier by said second signal of said second pair of quadrature signals;
    (e) first signal producing means for producing a first sum signal from output signals of said fourth and fifth multipliers and a first difference signal from output signals of said third and sixth multipliers; and
    (f) first mean frequency detecting means for detecting a mean frequency between said first sum and difference signals.

4. An ultrasonic Doppler blood flow velocity detection apparatus as claimed in claim 2, wherein said second Doppler signal detecting means comprises:
    (a) a third multiplier for multiplying an output signal of said first multiplier by first signal of said second pair of quadrature signals;
    (b) a fourth multiplier for multiplying an output signal of said first multiplier by a second signal of said second pair of quadrature signals;
    (c) a fifth multiplier for multiplying an output signal of said second multiplier by said first signal of said second pair of quadrature signals;
    (d) a sixth multiplier for multiplying an output signal of said second multiplier by said second signal of said second pair of quadrature signals;
    (e) second signal producing means for producing a second sum signal from output signals of said third and sixth multipliers and a second difference signal from output signals of said fourth and fifth multipliers; and
    (f) second mean frequency detecting means for detecting a mean frequency between said second sum and difference signals.

5. An ultrasonic Doppler blood flow detection apparatus as claimed in claim 1, wherein said frequency f2 is lower than a half of said frequency f1.

6. An ultrasonic Doppler blood flow velocity detection apparatus comprising:
    (a) signal producing means responsive to a clock signal for producing pulses at a predetermined interval, and for producing first and second pairs of quadrature signals having different frequencies f1 and f2 respectively;
    (b) transducing means for transmitting ultrasonic waves in response to each of said pulses and for receiving reflected ultrasonic waves from an ultrasonic-wave reflective object in the blood of a human body and converting the received ultrasonic waves into an electric echo signal;
    (c) frequency-difference component producing means responsive to said echo signal and said first pair of quadrature signals for producing frequency-difference components indicative of frequency differences between said echo signal and each of said first pair of quadrature signals respectively, said frequency-difference component producing means including first and second multipliers for multiplying said echo signal by said first pair of quadrature signals, respectively;
    (d) first Doppler signal detecting means for detecting a Doppler signal in a given frequency range within an upper sideband of said frequency f1 from said frequency-difference components in response to said second pair of quadrature signals;

(e) second Doppler signal detecting means for detecting a Doppler signal in another given frequency range within an lower sideband of said frequency f2 from said frequency-difference components in response to said second pair of quadrature signals; and (f) frequency difference calculating means for calculating frequency difference between output signals from said first and second Doppler signal detecting means.

7. An ultrasonic Doppler blood flow velocity detection apparatus as claimed in claim 6, wherein said first Doppler signal detecting means comprises:

(a) a third multiplier for multiplying an output signal of said first multiplier by a first signal of said second pair of quadrature signals;

(b) a fourth multiplier for multiplying an output signal of said first multiplier by a second signal of said second pair of quadrature signals;

(c) a fifth multiplier for multiplying an output signal of said second multiplier by said first signal of said second pair of quadrature signals;

(d) a sixth multiplier for multiplying an output signal of said second multiplier by said second signal of said second pair of quadrature signals;

(e) first signal producing means for producing a first sum signal from output signals of said fourth and fifth multipliers and a first difference signal from output signals of said third and sixth multipliers; and (f) first mean frequency detecting means for detecting a mean frequency between said first sum and difference signals.

8. An ultrasonic Doppler blood flow velocity detection apparatus as claimed in claim 6, wherein said second Doppler signal detecting means comprises:

(a) a third multiplier for multiplying an output signal of said first multiplier by first signal of said second pair of quadrature signals;

(b) a fourth multiplier for multiplying an output signal of said first multiplier by a second signal of said second pair of quadrature signals;

(c) a fifth multiplier for multiplying an output signal of said second multiplier by said first signal of said second pair of quadrature signals;

(d) a sixth multiplier for multiplying an output signal of said second multiplier by said second signal of said second pair of quadrature signals;

(e) signal producing means for producing a sum signal from output signals of said third and sixth multipliers and a second difference signal from output signals of said fourth and fifth multipliers; and (f) mean frequency detecting means for detecting a mean frequency between said second sum and difference signals.

9. An ultrasonic Doppler blood flow velocity detection apparatus comprising:

(a) signal producing means responsive to a clock signal for producing pulses at a predetermined interval, and for producing first and second pairs of quadrature signals having different frequencies f1 and f2 respectively;

(b) transducing means for transmitting ultrasonic waves in response to each of said pulses and for receiving reflected ultrasonic waves from an ultrasonic-wave reflective object in the blood of a human body and converting the received ultrasonic waves into an electric echo signal;

(c) frequency-difference component producing means responsive to said echo signal and said first pair of quadrature signals for producing frequency-difference components indicative of frequency differences between said echo signal and each of said first pair of quadrature signals respectively;

(d) first Doppler signal detecting means for detecting a Doppler signal in a given frequency range within an upper sideband of said frequency f1 from said frequency-difference components in response to said second pair of quadrature signals;

(e) second Doppler signal detecting means for detecting a Doppler signal in another given frequency range within an lower sideband of said frequency f2 from said frequency-difference components in response to said second pair of quadrature signals; and (f) frequency difference calculating means for calculating a frequency difference between output signals from said first and second Doppler signal detecting means, wherein said frequency f2 is lower than a half of said frequency f1.

* * * * *